United States Patent [19]

Misslitz et al.

[11] Patent Number: 5,496,792
[45] Date of Patent: Mar. 5, 1996

[54] CYCLOHEXENONE OXIDE ETHERS AND USE THEREOF AS HERBICIDES

[75] Inventors: Ulf Misslitz, Neustadt; Norbert Meyer, Ladenburg; Juergen Kast, Boehl-Iggelheim; Kaspar Bott, Mannheim; Helmut Walter, Obrigheim; Karl-Otto Westphalen, Speyer; Uwe Kardorff, Mannheim; Matthias Gerber, Mutterstadt, all of Germany

[73] Assignee: BASF Aktiengesellschaft, Ludwigshafen, Germany

[21] Appl. No.: 290,725

[22] PCT Filed: Jan. 30, 1993

[86] PCT No.: PCT/EP93/00215

§ 371 Date: Aug. 11, 1994

§ 102(e) Date: Aug. 11, 1994

[87] PCT Pub. No.: WO93/16063

PCT Pub. Date: Aug. 19, 1993

[30] Foreign Application Priority Data

Feb. 13, 1992 [DE] Germany .......................... 42 04 205.4

[51] Int. Cl.⁶ ........................... A01N 43/56; C07D 231/12
[52] U.S. Cl. ........................... 504/100; 504/271; 504/280; 504/288; 504/289; 504/292; 504/294; 504/343; 548/235; 548/247; 548/373.1; 548/377.1; 549/13; 549/75; 549/426; 549/491; 546/254; 564/256
[58] Field of Search ................... 504/100, 343, 504/280, 271, 288, 292, 294, 289; 548/235, 377.1, 373.1, 247; 549/13, 426, 492, 491, 75; 546/254; 564/256

[56] References Cited

U.S. PATENT DOCUMENTS

| 4,440,566 | 4/1984 | Luo | 71/98 |
| 5,190,573 | 3/1993 | Misslitz et al. | 504/292 |

FOREIGN PATENT DOCUMENTS

| 080301 | 6/1983 | European Pat. Off. . |
| 125094 | 11/1984 | European Pat. Off. . |
| 238021 | 9/1987 | European Pat. Off. . |
| 456112 | 11/1991 | European Pat. Off. . |
| 3838309 | 11/1988 | Germany . |

Primary Examiner—Jacqueline Haley
Attorney, Agent, or Firm—Keil & Weinkauf

[57] ABSTRACT

Cyclohexenone oxime ethers I

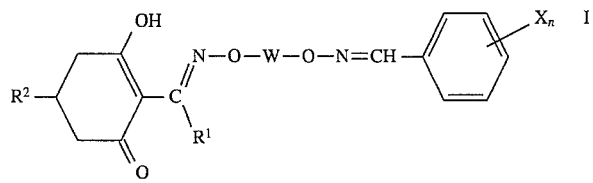

$R^1 = C_1$–$C_6$-alkyl; W= unsubstituted or $C_1$–$C_3$-alkyl-substituted $C_2$–$C_4$-alkylene chain;

X= $NO_2$, CN, halogen, $C_1$–$C_4$-alkyl, $C_1$–$C_4$-haloalkyl; n=0–3 or 1–5 if all X's are halogen;

$R^2$ = $C_1$–$C_4$-alkoxy-$C_1$–$C_6$-alkyl, $C_1$–$C_4$-alkylthio-$C_1$–$C_6$-alkyl, substituted or unsubstituted $C_3$–$C_7$-cycloalkyl, substituted or unsubstituted $C_5$–$C_7$-cycloalkenyl, a substituted or unsubstituted 5-membered saturated heterocycle containing 1 or 2 oxygen and/or sulfur atoms, substituted or unsubstituted 6- or 7-membered heterocycle having 1 or 2 non-adjacent oxygen and/or sulfur atoms and which is saturated or mono- or diunsaturated, substituted or unsubstituted 5-membered heteroaromatic containing 1 or 2N atoms and one O or S atom, phenyl or pyridyl, both of which are unsubstituted or bear 1–3 halogen, $NO_2$, CN, alkyl, alkoxy, alkyl-thio, haloalkyl, alkenyloxy, alkynyloxy and/or —$NR^aR^b$ substituents;

$R^a$= H, alkyl, alkenyl or alkynyl and $R^b$= H, alkyl, alkenyl, alkynyl, acyl or substituted or unsubstituted benzoyl;

and agriculturally utilizable salts and esters of compounds I with $C_1$–$C_{10}$-carboxylic acids and inorganic acids.

6 Claims, No Drawings

CYCLOHEXENONE OXIDE ETHERS AND USE THEREOF AS HERBICIDES

This application is a National Stage Application of PCT/EP93/00215 filed 30 Jan. 1993, now WO93/16063, published 19 Aug. 1993.

The present invention relates to novel cyclohexenone oxime ethers of the general formula I

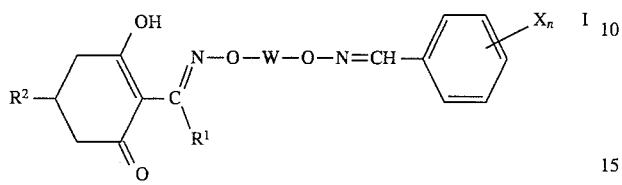

where:
$R^1$ is $C_1$–$C_6$-alkyl;
W is a $C_2$–$C_3$-alkylene chain, if desired substituted by $C_1$–$C_3$-alkyl;
X is nitro, cyano, halogen, $C_1$–$C_4$-alkyl or $C_1$–$C_4$-haloalkyl;
n is 0 to 3, where the radicals X can be different if n is 2 or 3, or 1 to 5 if all the Xs are halogen;
$R^2$ is $C_1$–$C_4$-alkoxy-$C_1$–$C_6$-alkyl or $C_1$–$C_4$-alkylthio-$C_1$–$C_6$-alkyl; $C_3$–$C_7$-cycloalkyl or $C_5$–$C_7$-cycloalkenyl, it being possible if desired for these groups to carry one to three substituents selected from a group consisting of $C_1$–$C_4$-alkyl, $C_1$–$C_4$-alkoxy, $C_1$–$C_4$-alkylthio, $C_1$–$C_4$-haloalkyl, hydroxyl and halogen; a 5-membered saturated heterocycle which consists of one or two oxygen and/or sulfur atoms as hetero atoms and which can, if desired, additionally carry one to three substituents selected from a group consisting of $C_1$–$C_4$-alkyl, $C_1$–$C_4$-alkoxy, $C_1$–$C_4$-alkylthio and $C_1$–$C_4$-haloalkyl; a 6- or 7-membered heterocycle having one or two non-adjacent oxygen and/or sulfur atoms as hetero atoms which can be saturated or mono- or diunsaturated, it being possible if desired for the heterocycle additionally to carry one to three substituents selected from a group consisting of hydroxyl, halogen, $C_1$–$C_4$-alkyl, $C_1$–$C_4$-alkoxy, $C_1$–$C_4$-alkylthio and $C_1$–$C_4$-haloalkyl, a 5-membered heteroaromatic, containing one or two nitrogen atoms and an oxygen or sulfur atom, it being possible for this ring if desired additionally to carry one to three substituents selected from a group consisting of halogen, cyano, $C_1$–$C_4$-alkyl, $C_1$–$C_4$-alkoxy, $C_1$–$C_4$-alkylthio, $C_1$–$C_4$-haloalkyl, $C_2$–$C_6$-alkenyl, $C_2$–$C_6$-alkenyloxy and $C_1$–$C_4$-alkoxy-$C_1$–$C_4$-alkyl; phenyl or pyridyl, it being possible for these groups if desired additionally to carry one to three of the following substituents selected from a group consisting of halogen, nitro, cyano, $C_1$–$C_4$-alkyl, $C_1$–$C_4$-alkoxy, $C_1$–$C_4$-alkylthio, $C_1$–$C_4$-haloalkyl, $C_3$–$C_6$-alkenyloxy, $C_3$–$C_6$-alkynyloxy and an amino group —$NR^aR^b$, where
$R^a$ is hydrogen, $C_1$–$C_4$-alkyl, $C_3$–$C_6$-alkenyl or $C_3$–$C_6$-alkynyl and
$R^b$ is hydrogen, $C_1$–$C_4$-alkyl, $C_3$–$C_6$-alkenyl, $C_3$–$C_6$-alkynyl, $C_1$–$C_6$-acyl or benzoyl which if desired can in turn additionally carry one to three radicals selected from a group consisting of nitro, cyano, halogen, $C_1$–$C_4$-alkyl, $C_1$–$C_4$-alkoxy, $C_1$–$C_4$-alkylthio and $C_1$–$C_4$-haloalkyl; and the agriculturally utilizable salts and esters of $C_1$–$C_{10}$-carboxylic acids and inorganic acids of the compounds I.

The invention additionally relates to a process for-preparing these compounds, their use as herbicides and herbicidal agents which contain these compounds as active substances.

In addition, the invention relates to novel hydroxylamines of the formula III

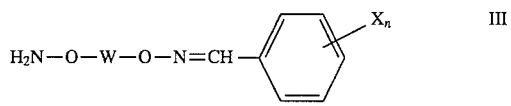

where
W is a $C_2$–$C_4$-alkylene chain which, if desired, is substituted by $C_1$–$C_3$-alkyl;
X is nitro, cyano, halogen, $C_1$–$C_4$-alkyl or $C_1$–$C_4$-haloalkyl and
n is 0 to 3, where the radicals X can be different if n is 2 or 3, or i to 5 if all the Xs are halogen.

Herbicidally active cyclohexanediones of the formula I'

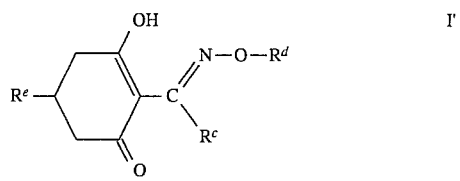

are already known from the literature, where $R^c$, $R^d$ and $R^e$ have, inter alia, the following meanings:

U.S. Pat. No. 4,440,566 ($R^c$= ethyl or propyl; $R^d$= benzyl; $R^e$=2-ethylthiopropyl);

EP-A 238,021 and EP-A 125,094 ($R^c$= ethyl or propyl; $R^d$= benzyl or but-2-enyl; $R^e$= a substituted 5-membered heteroaryl radical);

EP-A 80,301 ($R^c$= ethyl or propyl; $R^d$= benzyl or but-2-enyl; $R^e$= substituted phenyl);

DE-A 3,838,309 ($R^c$= ethyl or propyl; $R^d$= a substituted 4-phenylbutylene or 4-phenylbutenylene radical; $R^e$= a substituted 5- to 7-membered heterocycle);

EP-A 456,112 ($R^c$= ethyl or propyl; $R^d$= a substituted 3-phenoxypropylene or 2-phenoxyethylene radical; $R^e$= a substituted 5- to 7-membered heterocycle).

The herbicidal properties of these compounds, in particular with respect to their selectivity for weeds in graminaceous crop plants, however, may only give limited satisfaction.

Hence, it was an object of the present invention to provide novel cyclohexenone oxime ethers having improved selectivity for weeds in graminaceous crops such as rice and maize.

We have found that this object is achieved by the cyclohexenone oxime ethers I defined at the beginning. We have additionally found herbicidal compositions which contain these mixtures.

The cyclohexenone oxime ethers I are obtainable in various ways, namely preferably in a conventional manner from known cyclohexenones of the formula II (DE-A 3,838,309, EP-A 456,112) and the novel hydroxylamines of the formula III:

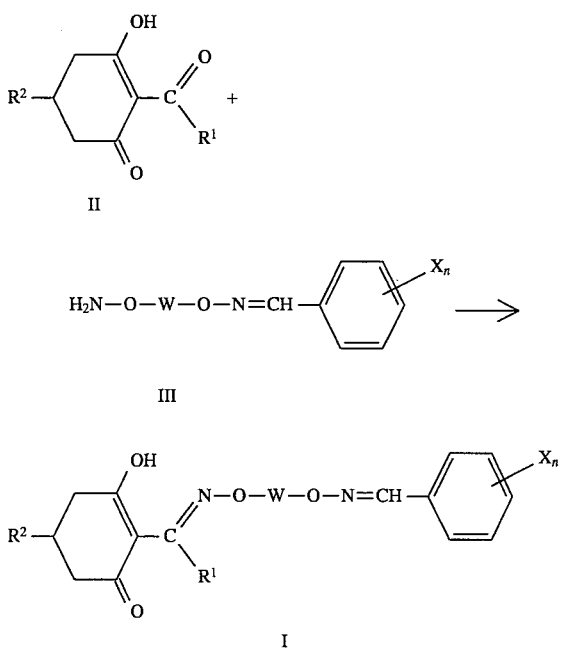

A suitable salt of the hydroxylamine III is preferably used, in particular its hydrochloride, and the reaction is carried out in the heterogeneous phase in an inert solvent, for example in dimethyl sulfoxide, in an alcohol such as methanol, ethanol and isopropanol, in an aromatic hydrocarbon such as benzene and toluene, in a chlorinated hydrocarbon such as chloroform and 1,2-dichloroethane, in an aliphatic hydrocarbon such as hexane and cyclohexane, in an ester such as ethyl acetate or in an ether such as diethyl ether, dioxane and tetrahydrofuran.

The reaction is conducted in the presence of a base, an amount of base of about 0.5 to 2 molar equivalents, based on the ammonium compound, normally being sufficient.

Suitable bases are, for example, carbonates, hydrogen carbonates, acetates, alkoxides or oxides of alkali metals or alkaline earth metals, in particular sodium hydroxide, potassium hydroxide, magnesium oxide or calcium oxide. Organic bases such as pyridine and tertiary amines such as triethylamine are additionally suitable.

The reaction is preferably carried out in methanol using sodium hydrogen carbonate as a base.

A variant of the process consists in carrying out the reaction without base with the free hydroxylamine base III, for example in the form of an aqueous solution; depending on the solvent used for the compound II, a single-phase or two-phase reaction mixture is obtained.

Suitable solvents for this variant are, for example, alcohols such as methanol, ethanol, isopropanol and cyclohexanol, aliphatic and aromatic, unchlorinated or chlorinated hydrocarbons such as hexane, cyclohexane, methylene chloride, toluene and dichloroethane, esters such as ethyl acetate, nitriles such as acetonitrile and cyclic ethers such as dioxane and tetrahydrofuran.

The cyclohexenone II and the hydroxylamine III or its salt are expediently employed in an approximately stoichiometric ratio, but in some cases an excess of one or the other components, up to about 10 mol %, can also be advantageous.

The reaction temperature is in general from 0° C. to the boiling point of the reaction mixture, preferably from 20° to 80° C.

The reaction is complete after a few hours. The product can be isolated in a customary manner, for example by concentrating the mixture, partitioning the residue in methylene chloride/water and distilling off the solvent under reduced pressure.

Particular requirements with respect to the pressure do not have to be taken into account; in general, the reaction is therefore carried out at atmospheric pressure or under the autogenous pressure of the respective diluent.

On account of their acidic character, the cyclohexenone oxime ethers I according to the invention can form salts of alkali metal or alkaline earth metal compounds, as well as enol esters.

Alkali metal salts of the compounds I can be obtained by treating the 3-hydroxycyclohexenone compounds with sodium hydroxide or alkoxide or potassium hydroxide or alkoxide in aqueous solution or in an organic solvent such as methanol, ethanol, acetone or toluene.

Other metal salts such as manganese, copper, zinc, iron, calcium, magnesium and barium salts can also be prepared from the sodium salts in a customary manner, as well as ammonium and phosphonium salts by means of ammonia, or phosphonium, sulfonium or sulfoxonium hydroxides.

The esters of the compounds I are also obtainable in a customary manner (cf., for example, Organikum, VEB Deutscher Verlag der Wissenschaften, Berlin, 17th edition, (1988) pp. 405–408).

The novel hydroxylamines of the formula III

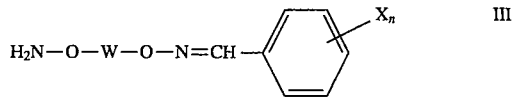

where

W is a $C_2$–$C_4$-alkylene chain which, if desired, is substituted by $C_1$–$C_3$-alkyl;

X is nitro, cyano, halogen, $C_1$–$C_4$-alkyl or $C_1$–$C_4$-haloalkyl and n is 0 to 3, where the radicals X can be different if n is 2 or 3, or i to 5 if all the Xs are halogen, can as a rule be prepared by a number of known process steps starting from known precursors. Preferably, a I ω-bis(aminooxy)alkane IV (Angew. Makromol. Chem. 184, (1985); Bioorg. Khim. 11, 1574 (1985); J. Org. Chem. 54, 2351 (1989) in a manner known for hydroxylamines (Houben-Weyl, Methods of organic chemistry vol. E 14b, pp. 369) is coupled with an aldehyde V with elimination of water to give the hydroxylamine derivative III:

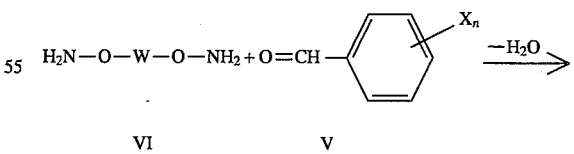

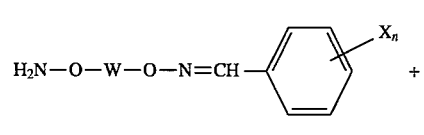

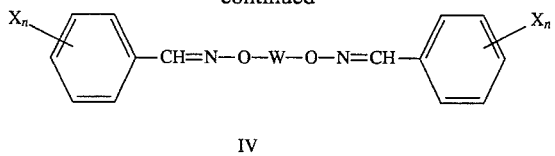

IV

The 1, ω-bis(benzylideneiminoxy)alkanes VI occur as by-products.

The hydroxylamines III can be isolated from the reaction mixtures obtained by these processes by means of customary working-up methods, for example by extraction or by crystallization. To increase the tendency of these hydroxylamine derivatives to crystallize, it may be advantageous to convert these into the salts of inorganic acids or organic acids. To this end, dilute solutions of these acids are generally reacted with the hydroxylamines III, namely expediently approximately equivalent amounts of acid and hydroxylamine III.

Like the hydroxylamines III having a free amino group, the hydroxylammonium salts obtained can be processed directly to give the herbicides of the formula I or alternatively stored, if desired.

The cyclohexenone oxime ethers I can be obtained during the preparation as isomer mixtures, both E/Z isomer mixtures and enantiomer or diastereoisomer mixtures being possible. If desired, the isomer mixtures can be separated by the methods customary for this purpose, for example by chromatography or by crystallization.

The cyclohexenone oxime ethers I can be written in several tautomeric forms, which are all included by the invention.

The collective terms used in the definitions of the substituents halogen, $C_1-C_4$-alkyl, $C_1-C_4$-alkoxy, $C_1-C_4$-alkylthio, $C_1-C_4$-haloalkyl, $C_2-C_6$-alkenyl, $C_2-C_6$-alkenyloxy, $C_3-C_6$-alkenyl, $C_3-C_6$-alkenyloxy, $C_3-C_6$-alkynyl, $C_3-C_6$-alkynyloxy, $C_1-C_6$-acyl are a short way of writing an individual list of the individual group members. All the alkyl, alkoxy, alkylthio, haloalkyl, alkenyl, alkenyloxy, alkynyl and alkynyloxy moieties can be straight-chain or branched. The haloalkyl moieties can carry identical or different halogen atoms.

The following terms specifically mean, for example halogen: fluorine, chlorine, bromine and iodine;

$C_1-C_4$-alkyl: methyl, ethyl, n-propyl, 1-methylethyl, n-butyl, 1-methylpropyl, 2-methylpropyl and 1,1-dimethylethyl;

$C_1-C_4$-alkoxy: methoxy, ethoxy, n-propoxy, 1-methylethoxy, n-butoxy, 1-methylpropoxy, 2-methylpropoxy and 1,1-dimethylethoxy;

$C_1-C_4$-alkylthio: methylthio, ethylthio, n-propylthio, 1-methylethylthio, n-butylthio, 1-methylpropylthio, 2-methylpropylthio and 1,1-dimethylethylthio; $C_1-C_4$-haloalkyl: fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl; $C_2-C_6$-alkenyl: ethenyl and $C_3-C_6$-alkenyl such as 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl; $C_2-C_6$-alkenyloxy: ethenyloxy and $C_3-C_6$-alkenyloxy such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy and 1-ethyl-2-methyl-2-propenyloxy;

With respect to biological activity, cyclohexenones of the formula I are preferred in which the substituents have the following meanings:

$R^1$ $C_1-C_6$-alkyl such as methyl, ethyl, n-propyl, n-butyl, n-pentyl, n-hexyl, in particular ethyl and propyl;

W is $C_2-C_4$-alkylene, such as ethylene, propylene butylene, which can be substituted by one to three methyl or ethyl radicals. Ethylene, propylene, and 2-methylpropylene, 2,2-dimethylpropylene butylene are particularly preferred;

X—nitro, cyano,
halogen, in particular fluorine, chlorine and bromine;
$C_1-C_4$-alkyl, in particular methyl;
$C_1-C_4$-haloalkyl, in particular difluoromethyl, trifluoromethyl, 2,2,2-trifluoroethyl and pentafluoroethyl;
halogen is particularly preferred;

n is 0 to 3, where the radicals X can be different if n is 2 or 3, or 1 to 5 if all the Xs are halogen; n is particularly preferably 1 to 3;

$R^2$ $C_1$–$C_6$-alkyl such as methyl, ethyl, propyl, 1-methylethyl, n-butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, where the alkyl is substituted by $C_1$–$C_4$-alkoxy, in particular methoxy, ethoxy, 1-methylethoxy or 1,1-dimethylethoxy, or by $C_1$–$C_4$-alkylthio, in particular methylthio or ethylthio, namely preferably in the 1-, 2 - or 3-position; 2-ethylthiopropyl is very particularly preferred; $C_3$–$C_7$-cycloalkyl or $C_5$–$C_7$-cycloalkenyl such as cyclopropyl, cyclobutyl, cyclopentyl, cyclohexyl, cycloheptyl, cyclopentenyl, cyclohexenyl and cycloheptenyl, where these groups can carry one to three of the following substituents: $C_1$–$C_4$-alkyl $C_1$–$C_4$-alkoxy, $C_1$–$C_4$-alkylthio or $C_1$–$C_4$-haloalkyl; 1-methylthio-1-cyclopropyl is very particularly preferred; a 5-membered saturated heterocycle such as tetrahydrofuranyl, tetrahydrothienyl, dioxolanyl, dithiolanyl and oxathiolanyl, in particular tetrahydrofuranyl, tetrahydrothienyl and dioxolanyl, where these rings can be unsubstituted or can carry one to three substituents selected from a group consisting of $C_1$–$C_4$-alkyl, $C_1$–$C_4$-alkoxy, $C_1$–$C_4$-alkylthio and $C_1$–$C_4$-haloalkyl s a 5 -membered heteroaromatic such as pyrrolyl, pyrazolyl, imidazolyl, isoxazolyl, oxazolyl, isothiazolyl, thiazolyl, furanyl and thienyl, in particular isoxazolyl and furanyl, where the 5-membered heteroaromatic can in each case be unsubstituted or can carry one to three substituents selected from a group consisting of $C_1$–$C_4$-alkyl, $C_1$–$C_4$-alkoxy, $C_1$–$C_4$-alkylthio, $C_1$–$C_4$-haloalkyl, $C_1$–$C_4$-alkoxy-$C_1$–$C_4$-alkyl such as methoxymethyl, 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 2-ethoxy-1-methylethyl and 1-ethoxy- 1-methylethyl, in particular methoxyethyl and ethoxyethyl, $C_2$–$C_6$-alkenyl such as ethenyl and $C_3$–$C_6$-alkenyl, $C_2$–$C_6$- alkenyloxy such as ethenyloxy and $C_3$–$C_6$-alkenyloxy, in particular 1-methylethen-1-yloxy, a 6- or 7-membered heterocycle which a) can be saturated, for example tetrahydropyran- 3-yl, tetrahydropyran-4-yl, tetrahydrothiopyran- 3-yl, tetrahydrothiopyran-4-yl and dioxepan-5-yl, b) can be mono- or diunsaturated, for example dihydropyran-3-yl, dihydropyran-4-yl, dihydrothiopyran- 3-yl and dihydrothiopyran-4-yl, where the heterocycles can be unsubstituted or can carry one to three substituents selected from a group consisting of hydroxyl, halogen, $C_1$–$C_4$-alkyl, $C_1$–$C_4$-alkoxy, $C_1$–$C_4$-alkylthio and $C_1$–$C_4$-haloalkyl; tetrahydropyran-3-yl, tetrahydropyran-4-yl and tetrahydrothiopyran-3-yl are very particularly preferred; phenyl or pyridyl, both of which can be unsubstituted or can carry one to three substituents selected from a group consisting of $C_1$–$C_4$-alkyl, $C_1$–$C_4$-alkoxy, $C_1$–$C_4$-alkylthio, $C_1$–$C_4$-haloalkyl, $C_3$–$C_6$-alkenyloxy, $C_3$–$C_6$-alkynyloxy such as 2-propynyloxy, 2-butynyloxy, 3-butynyloxy, 1-methyl- 2-propynyloxy, 2-pentynyloxy, 3-pentynyloxy, 4-pentynyloxy, 1-methyl-3-butynyloxy, 2-methyl- 3-butynyloxy, 1-methyl-2-butynyloxy, 1,1-dimethyl- 2-propynyloxy, 1-ethyl-2-propynyloxy, 2-hexynyloxy, 3-hexynyloxy, 4-hexynyloxy, 5-hexynyloxy, 1-methyl- 2-pentynyloxy, 1-methyl-3-pentynyloxy, 1-methyl- 4-pentynyloxy, 2-methyl-3-pentynyloxy, 2-methyl- 4-pentynyloxy, 3-methyl-4-pentynyloxy, 4-methyl-2-pentynyloxy, 1,1-dimethyl-2-butynyloxy, 1,1-dimethyl- 3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy and 1-ethyl-1-methyl-2-propynyloxy, preferably 2-propynyloxy and 2-butynyloxy; one of the three substituents on the phenyl or pyridyl ring can also be an amino group —$NR^aR^b$, where $R^a$ is hydrogen, $C_1$–$C_4$-alkyl, in particular methyl or ethyl, $C_3$–$C_6$-alkenyl, in particular 2-propenyl or 2-butenyl, $C_3$–$C_6$-alkynyl, in particular 2-propynyl or 2-butynyl, and $R^b$ is hydrogen, $C_1$–$C_4$-alkyl, in particular methyl or ethyl, $C_3$–$C_6$-alkenyl, in particular 2-propenyl or 2-butenyl, $C_3$–$C_6$-alkynyl, in particular 2-proplynyl or 2-butynyl, or is $C_1$–$C_6$-acyl such as acetyl, propionyl, n-butyryl, 2-methylpropionyl, n-pentanoyl, 2-methylbutynyl, 3-methylbutyryl, 2,2-dimethylpropionyl, n-hexanoyl, 2-methylpentanoyl, 3-methylpentanoyl, 4-methylpentanoyl, 2,2-dimethylbutyryl, 2,3-dimethylbutyryl, 3,3-dimethylbutyryl and 2-ethylbutyryl, n particular acetyl or propionyl, or benzoyl which can be in turn unsubstituted or can carry one to three radicals selected from a group consisting of nitro, cyano, halogen, preferably fluorine, chlorine or bromine, $C_1$–$C_4$-alkyl, preferably methyl, $C_1$–$C_4$-alkoxy, preferably methoxy or ethoxy, $C_1$–$C_4$-alkylthio, preferably methylthio, or $C_1$–$C_4$-haloalkyl, preferably trifluoromethyl.

Suitable salts of the compounds of the formula I are agriculturally utilizable salts, for example alkali metal salts, in particular the sodium or potassium salt, alkaline earth metal salts, in particular the calcium, magnesium or barium salt, the manganese, copper, zinc or iron salt or the ammonium, phosphonium, sulfonium or sulfoxonium salts, for example ammonium salts, tetraalkylammonium salts, benzyltrialkylammonium salts, trialkylsulfonium salts or trialkylsulfoxonium salts.

Esters of $C_1$–$C_{10}$-carboxylic acids are in particular understood as meaning $C_1$–$C_6$-alkanecarboxylic acids such as methanecarboxylic acid (acetic acid), ethanecarboxylic acid (propionic acid), propanecarboxylic acid (burytic acid), 1-methylethanecarboxylic acid (isobutyric acid), butanecarboxylic acid, 1-methylpropanecarboxylic acid, 2-methylpropanecarboxylic acid, 1,1-dimethylethanecarboxylic acid, pentanecarboxylic acid, 1-methylbutanecarboxylic acid, 2-methylbutanecarboxylic acid, 3-methylbutanecarboxylic acid, 1,1-dimethylpropanecarboxylic acid, 1,2-dimethylpropanecarboxylic acid, 2,2-dimethylpropanecarboxylic acid, 1-ethylpropanecarboxylic acid, benzoic acid and benzoic acids substituted by halogen, hexanecarboxylic acid, 1-methylpentanecarboxylic acid, 2-methylpentanecarboxylic acid, 3-methylpentanecarboxylic acid, 4-methylpentanecarboxylic acid, 1,1-dimethylbutanecarboxylic acid, 1,2-dimethylbutanecarboxylic acid, 1,3-dimethylbutanecarboxylic acid, 2,2-dimethylbutanecarboxylic acid, 2,3-dimethylbutanecarboxylic acid, 3,3-dimethylbutanecarboxylic acid, 1-ethylbutanecarboxylic acid, 2-ethylbutanecarboxylic acid, 1,1,2-trimethylpropanecarboxylic acid, 1,2,2-trimethylpropanecarboxylic acid, 1-ethyl-1-methylpropanecarboxylic acid and 1-ethyl-2-methylpropanecarboxylic acid.

PREPARATION EXAMPLES

2-[1-[[2-(4-fluorobenzylideniminooxy)ethoxy]imino]-propel]-3-hydroxy-5-(2H-tetrahydrothiopyran-3-yl)- 2-cyclohexen-1-one A mixture of 3.0 g (11 mmol) of 3-hydroxy-2-propionyl-5-(2H-tetrahydrothiopyran-3-yl)-2-cyclohexen- 1-one, 2,6 g (13 mmol) of O-[2-(4-flurobenzylideneiminooxy)ethyl] hydroxylamine and 100 ml of methanol was stirred at 25° C. for 16 hours. The mixture was concentrated under reduced pressure and the residue was taken up in 100 ml of 10% strength by weight sodium hydroxide solution. The aqueous phase was extracted three times with 50 ml of methylene chloride each time, cooled to 0° C. and acidified to pH 1 with conc. hydrochloric acid. The mixture was then extracted with 100 ml of diethyl ether, after which the ether phase was dried over sodium sulfate, then filtered through silica gel and concentrated.

Yield: 45%;

$^1$H-NMR (200 MHz, CDCl$_3$): δ=1.15 ppm (t,3H); 1.50–2.60 ppm (m, 15H); 2.85 ppm (m, 2H); 4.35 ppm (m, 4H); 7.00 ppm (m, 2H); 7.55 ppm (m, 2H); 8.05 ppm (s,1H).

Precursor

O-[2-(4-fluorobenzylideniminooxy)ethyl]hydroxylamine 50 g (0.4 mol of 4-fluorobenzylaldehyde in 200 ml of methanol was added dropwise at 23°–35° C. in the course of 2 hours to a solution of 46 g (0.5 mol) of 1,2-bis-(aminooxy)ethane in 50 ml of methanol and the mixture was stirred at 20°–25° C. for 12 hours. After filtration*), the solution obtained was concentrated. The residue was taken up in 100 ml of diethyl ether, after which the organic phase was washed with water, dried over sodium sulfate, filtered through silica gel and finally

*The solid precipitated in the reaction was washed with methanol and petroleum ether and then dried. 12 g of 1,2-bis(4-fluorobenzylideniminooxy)ethane were obtained; melting point: 83°–85° C. concentrated again.

Yield= 56%;

$^1$H-NMR (200 MHz, in CDCl$_3$): δ= 3.93 ppm (m, 2H), 4.35 ppm (m, 2H), 5.50 ppm (bs,2H); 7.00 ppm (m, 2H); 7.45 ppm (m, 2H); 8.10 ppm (s,1H).

In Table I which follows, further hydroxylamines III are shown which were prepared or can be prepared in the same way. Tables 2 to 5 contain cyclohexenone oxime ethers I according to the invention.

TABLE 1

$$H_2N-O-W-O-N=CH-\text{C}_6\text{H}_4-X_n \quad \text{III}$$

| No. | W | $X_n$ | $^1$H-NMR data [ppm] |
|---|---|---|---|
| 1.01 | —CH$_2$CH$_2$— | — | 3.95(m, 2H); 4.35(m, 2H); 5.55(bs, 2H); 7.25–7.60(m, 5H); 8.15(s, 1H) |
| 1.02 | —CH$_2$CH$_2$— | 4-Cl | 3.95(m, 2H); 4.35(m, 2H); 5.55(bs, 2H); 7.20–7.55(m, 4H); 8.10 (s, 1H) |
| 1.03 | —CH$_2$CH$_2$— | 4-F | 3.93(m, 2H); 4.35(m, 2H); 5.50(bs, 2H); 7.0(m, 2H), 7.45(m, 2H); 8.10(s, 1H) |
| 1.04 | —CH$_2$CH$_2$— | 3,4-Cl$_2$ | 3.95(m, 2H); 4.35(m, 2H); 5.55(bs, 2H); 7.40(m, 2H); 7.65(m, 1H); 8.05(s, 1H) |
| 1.05 | —CH$_2$CH$_2$— | 2,4-Cl$_2$ | 3.95(m, 2H); 4.38(m, 2H); 5.55(bs, 2H); 7.20(m, 1H); 7.35(m, 1H); 7.80(m, 1H); 8.45(s, 1H) |
| 1.06 | —CH$_2$CH$_2$— | 4-NO$_2$ | 3.98(m, 2H); 4.40(m, 2H); 5.60(bs, 2H); 7.75(m, 2H); 8.25(m, 3H) |
| 1.07 | —CH$_2$CH$_2$CH$_2$CH$_2$— | — | 1.75(m, 4H); 3.70(t, 2H); 4.20(t, 2H); 5.30(bs, 2H); 7.35(m, 3H); 7.55(m, 2H); 8.05(s, 1H) |
| 1.08 | —CH$_2$CH$_2$CH$_2$CH$_2$— | 4-Cl | 1.70(m, 4H); 3.70(t, 2H); 4.15(t, 2H); 5.35(bs, 2H); 7.30(m, 2H); 7.45(m, 2H); 8.00(s, 1H) |
| 1.09 | —CH$_2$CHCH$_2$CH$_2$— | 4-F | 1.75(m, 4H); 3.70(t, 2H); 4.20(t, 2H); 5.35(bs, 2H); 7.05(m, 2H); 7.55(m, 2H); 8.05(s, 1H) |
| 1.10 | —CH$_2$CHCH$_2$CH$_2$— | 2,4-Cl$_2$ | 1.75(m, 4H); 3.70(t, 2H); 4.20(t, 2H); 5.35(bs, 2H); 7.25(m, 1H); 7.35(m, 1H); 7.70(m, 1H); 8.40(s, 1H) |
| 1.11 | —CH$_2$CH$_2$CH$_2$— | 2,4-Cl$_2$ | 2.00(m, 2H); 3.80(m, 2H); 4.25(m, 2H); 5.30(bs, 2H); 7.25(m, 1H); 7.35(m, 1H); 7.80(m, 1H); 8.40(s, 1H) |
| 1.12 | —CH$_2$CH$_2$CH$_2$— | 4-Cl | 2.00(m, 2H); 3.75(m, 2H); 4.25(m, 2H); 5.30(bs, 2H); 7.35(m, 2H); 7.55(m, 2H); 8.05(s, 1H) |
| 1.13 | —CH$_2$CH$_2$CH$_2$— | 4-F | 2.00(m, 2H); 3.75(m, 2H); 4.25(m, 2H); 5.20(bs, 2H); 7.05(m, 2H); 7.55(m, 2H); 8.05(s, 1H) |

TABLE 2

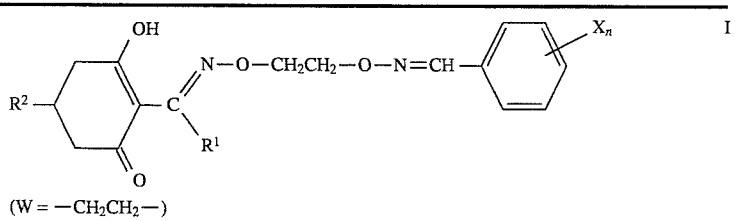

(W = —CH$_2$CH$_2$—)

| No. | R$^1$ | R$^2$ | $X_n$ | Phys. data ($^1$H-NMR [ppm], m.p. [°C.]) |
|---|---|---|---|---|
| 2.01 | Ethyl | Tetrahydrothiopyran-3-yl | — | 1.15(t, 3H); 4.50(m, 4H); 7.35 (m, 3H); 7.60(m, 2H); 8.15(s, 1H) |
| 2.02 | Propyl | Tetrahydrothiopyran-3-yl | — | 0.95(t, 3H); 4.50(m, 4H); 7.35 (m, 3H); 7.60(m, 2H); 8.15(s, 1H) |
| 2.03 | Ethyl | Tetrahydropyran-3-yl | — | 1.10(t, 3H); 4.35(m, 4H); 7.35 |

TABLE 2-continued $$\underset{(W = -CH_2CH_2-)}{R^2 \diagdown \text{cyclohexenone with OH, C(R}^1\text{)=N-O-CH}_2\text{CH}_2\text{-O-N=CH-C}_6\text{H}_{5-n}\text{X}_n}$$  I

| No. | R¹ | R² | X$_n$ | Phys. data (¹H-NMR [ppm], m.p. [°C.]) |
|---|---|---|---|---|
| 2.04 | Propyl | Tetrahydropyran-3-yl | — | (m, 3H); 7.55(m, 2H); 8.10(s, 1H); 0.95(t, 3H); 4.40(m, 4H); 7.35 (m, 3H); 7.60(m, 2H); 8.15(s, 1H); |
| 2.05 | Ethyl | Tetrahydropyran-4-yl | — | 1.10(t, 3H); 4.40(m, 4H); 7.35 (m, 3H); 7.60(m, 2H); 8.15(s, 1H) |
| 2.06 | Propyl | Tetrahydropyran-4-yl | — | 0.93(t, 3H); 4.40(m, 4H); 7.35 (m, 3H); 7.60(m, 2H); 8.15(s, 1H) |
| 2.07 | Ethyl | Tetrahydrothiopyran-3-yl | 4-Cl | 1.15(t, 3H); 4.35(m, 4H); 7.30 (m, 2H); 7.45(m, 2H); 8.05(s, 1H) |
| 2.08 | Propyl | Tetrahydrothiopyran-3-yl | 4-Cl | 1.05(t, 3H); 4.35(m, 4H); 7.30 (m, 2H); 7.45(m, 2H); 8.05(s, 1H) |
| 2.09 | Ethyl | Tetrahydropyran-3-yl | 4-Cl | 1.05(t, 3H); 4.35(m, 4H); 7.40 (m, 2H); 7.50(m, 2H); 8.05(s, 1H) |
| 2.10 | Propyl | Tetrahydropyran-3-yl | 4-Cl | 0.85(t, 3H); 4.35(m, 4H); 7,.30 (m, 2H); 7.50(m, 2H); 8.05(s, 1H) |
| 2.11 | Ethyl | Tetrahydropyran-4-yl | 4-Cl | 76–79 |
| 2.12 | Propyl | Tetrahydropyran-4-yl | 4-Cl | 0.90(t, 3H); 4.40(m, 4H); 7.30 (m, 2H); 7.50(m, 2H); 8.05(s, 1H); |
| 2.13 | Ethyl | Tetrahydrothiopyran-3-yl | 4-F | 1.15(t, 3H); 4.35(m, 4H); 7.00 (m, 2H); 7.55(m, 2H); 8.05(s, 1H) |
| 2.14 | Propyl | Tetrahydrothiopyran-3-yl | 4-F | 0.95(t, 3H); 4.35(m, 4H); 7.00 (m, 2H); 7.55(m, 2H); 8.05(s, 1H) |
| 2.15 | Ethyl | Tetrahydropyran-3-yl | 4-F | 1.10(t, 3H); 4.45(m, 4H); 7.05 (m, 2H); 7.55(m, 2H); 8.05(s, 1H) |
| 2.16 | Propyl | Tetrahydropyran-3-yl | 4-F | 0.95(t, 3H); 4.45(m, H); 7.05 (m, 2H); 7.55(m, 2H); 8.05(s, 1H) |
| 2.17 | Ethyl | Tetrahydropyran-4-yl | 4-F | 1.10(t, 3H); 4.35(m, 4H); 7.00 (m, 2H); 7.55(m, 2H); 8.05(s, 1H) |
| 2.18 | Propyl | Tetrahydropyran-4-yl | 4-F | 1.10(t, 3H); 4.35(m, 4H); 7.00 (m, 2H); 7.55(m, 2H); 8.05(s, 1H) |
| 2.19 | Ethyl | Tetrahydrothiopyran-3-yl | 2,4-Cl$_2$ | 1.15(t, 3H); 4.35(m, 4H); 7.20 (m, 2H); 7.35(m, 1H); 7.80(m, 1H); 18.45(s, 1H) |
| 2.20 | Propyl | Tetrahydrothiopyran-3-yl | 2,4-Cl$_2$ | 80–82 |
| 2.21 | Ethyl | Tetrahydropyran-3-yl | 2,4-Cl$_2$ | 1.10(m, 3H); 4.35(m, 4H); 7.20 (m, 2H); 7.40(m, 1H); 7.80(m, 1H); 8.50(s, 1H) |
| 2.22 | Propyl | Tetrahydropyran-3-yl | 2,4-Cl$_2$ | 0.95(m, 3H); 4.35(m, 4H); 7.15 (m, 2H); 7.35(m, 1H); 7.80(m, 1H); 8.45(s, 1H); |
| 2.23 | Ethyl | Tetrahydropyran-4-yl | 2,4-Cl$_2$ | 1.15(t, 3H); 4.40(m, 4H); 7.20 (s, 1H); 7.35(m, 1H); 7.80(m, 1H); 8.45(s, 1H) |
| 2.24 | Propyl | Tetrahydropyran-4-yl | 2,4-Cl$_2$ | 0.95(t, 3H); 4.40(m, 4H); 7.20 (s, 1H); 7.35(m, 1H); 7.80(m, 1H); 8.45(s, 1H) |
| 2.25 | Ethyl | Tetrahydrothiopyran-3-yl | 3,4-Cl$_2$ | 1.05(t, 3H); 4.40(m, 4H); 7.40 (m, 2H); 7.70(s, 1H); 8.00(s, 1H) |
| 2.26 | Propyl | Tetrahydrothiopyran-3-yl | 3,4-Cl$_2$ | 0.95(t, 3H); 4.40(m, 4H); 7.40 (m, 2H); 7.65(s, 1H); 8.00(s, 1H) |
| 2.27 | Ethyl | Tetrahydropyran-3-yl | 3,4-Cl$_2$ | 76–79 |
| 2.28 | Propyl | Tetrahydropyran-3-yl | 3,4-Cl$_2$ | 0.95(t, 3H); 4.35(m, 4H); 7.40 (m, 2H); 7.65(s, 1H); 8.05(s, 1H) |
| 2.29 | Ethyl | Tetrahydropyran-4-yl | 3,4-Cl$_2$ | 1.15(t, 3H); 4.40(m, 4H); 7.40 (m, 2H); 7.65(s, 1H); 8.05(s, 1H) |
| 2.30 | Propyl | Tetrahydropyran-4-yl | 3,4-Cl$_2$ | 0.95(t, 3H); 4.35(m, 4H); 7.40 (m, 2H); 7.65(s, 1H); 8.05(s, 1H) |
| 2.31 | Ethyl | Tetrahydrothiopyran-3-yl | 4-NO$_2$ | 110–112 |
| 2.32 | Propyl | Tetrahydrothiopyran-3-yl | 4-NO$_2$ | 88–90 |
| 2.33 | Ethyl | Tetrahydropyran-3-yl | 4-NO$_2$ | 110–112 |
| 2.34 | Propyl | Tetrahydropyran-3-yl | 4-NO$_2$ | 74–75 |
| 2.35 | Ethyl | Tetrahydropyran-4-yl | 4-NO$_2$ | 140–142 |
| 2.36 | Propyl | Tetrahydropyran-4-yl | 4-NO$_2$ | 96–98 |
| 2.37 | Propyl | 2-(Ethylthio)-1-propyl | | 1.25(d+t, 6H); 4.40(m, 4H); 7.35 (m, 3H); 7.60(m, 2H); 8.15(s, 1H) |
| 2.38 | Propyl | 2-(Ethylthio)-1-propyl | 4-Cl | 1.20(d+t, 6H); 4.40(m, 4H); 7.35 |

TABLE 2-continued $$\text{R}^2 \underset{\underset{O}{\parallel}}{\overset{OH}{\underset{C}{\bigcirc}}} \overset{N-O-CH_2CH_2-O-N=CH}{\underset{R^1}{\diagup}} \overset{X_n}{\bigcirc} \quad I$$

(W = —CH₂CH₂—)

| No. | R¹ | R² | X_n | Phys. data ($^1$H-NMR [ppm], m.p. [°C.]) |
|---|---|---|---|---|
| 2.39 | Propyl | 2-(Ethylthio)-1-propyl | 4-F | (m, 2H); 7.45(m, 2H); 8.07(s, 1H)<br>1.25(d+t, 6H); 4.40(m, 4H); 7.05<br>(m, 2H); 7.55(m, 2H); 8.10(s, 1H) |
| 2.40 | Propyl | 2-(Ethylthio)-1-propyl | 2,4-Cl₂ | 1.25(d+t, 6H); 4.40(m, 4H); 7.20<br>(m, 1H); 7.40(m, 1H); 7.80(m, 1H)<br>8.45(s, 1H) |
| 2.41 | Propyl | 2-(Ethylthio)-1-propyl | 3,4-Cl₂ | 1.25(d+t, 6H); 4.40(m, 4H); 7.40<br>(m, 2H); 7.70(m, 1H); 8.05(s, 1H) |
| 2.42 | Ethyl | 2,4,6-Trimethylphenyl | — | |
| 2.43 | Ethyl | 2,4,6-Trimethylphenyl | 4-Cl | 2.20(s, 3H); 2.35(s, 6H);<br>4.35(m, 4H); 6.85(s, 2H);<br>7.20–7.60(m, 4H); 8.10(s, 1H) |
| 2.44 | Ethyl | 2,4,6-Trimethylphenyl | 4-F | |
| 2.45 | Ethyl | 2,4,6-Trimethylphenyl | 2,4-Cl₂ | |
| 2.46 | Ethyl | 2,4,6-Trimethylphenyl | 3,4-Cl₂ | |
| 2.47 | Ethyl | 4-(Prop-2-ynyloxy)phenyl | — | |
| 2.48 | Ethyl | 4-(Prop-2-ynyloxy)phenyl | 4-Cl | |
| 2.49 | Ethyl | 4-(Prop-2-ynyloxy)phenyl | 4-F | |
| 2.50 | Ethyl | 4-(Prop-2-ynyloxy)phenyl | 2,4-Cl₂ | |
| 2.51 | Ethyl | 4-(Prop-2-ynyloxy)phenyl | 3,4-Cl₂ | |
| 2.52 | Ethyl | 1-Methylthio-1-cyclopropyl | — | |
| 2.53 | Ethyl | 1-Methylthio-1-cyclopropyl | 4-Cl | |
| 2.54 | Ethyl | 1-Methylthio-1-cyclopropyl | 4-F | |
| 2.55 | Ethyl | 1-Methylthio-1-cyclopropyl | 2,4-Cl₂ | |
| 2.56 | Ethyl | 1-Methylthio-1-cyclopropyl | 3,4-Cl₂ | |
| 2.57 | Ethyl | 1,3-Dimethylpyrazol-5-yl | — | |
| 2.58 | Ethyl | 1,3-Dimethylpyrazol-5-yl | 4-Cl | |
| 2.59 | Ethyl | 1,3-Dimethylpyrazol-5-yl | 4-F | |
| 2.60 | Ethyl | 1,3-Dimethylpyrazol-5-yl | 2,4-Cl₂ | |
| 2.61 | Ethyl | 1,3-Dimethylpyrazol-5-yl | 3,4-Cl₂ | |
| 2.62 | Propyl | 3-Isopropylisoxazol-5-yl | — | |
| 2.63 | Propyl | 3-Isopropylisoxazol-5-yl | 4-Cl | |
| 2.64 | Propyl | 3-Isopropylisoxazol-5-yl | 4-F | 1.15(d, 6H); 4.35(m, 2H); 5.90<br>(s, 1H); 7.05(m, 2H); 7.55(m, 2H);<br>8.10(s, 1H) |
| 2.65 | Propyl | 3-Isopropylisoxazol-5-yl | 2,4-Cl₂ | |
| 2.66 | Propyl | 3-Isopropylisoxazol-5-yl | 3,4-Cl₂ | |
| 2.67 | Propyl | Phenyl | 2,4-Cl₂ | 97–99 |
| 2.68 | Propyl | Thien-3-yl | 2,4-Cl₂ | 93–94 |
| 2.69 | Ethyl | 5,6-Dihydro-2H-thiopyran-3-yl | 2,4-Cl₂ | 84–85 |
| 2.70 | Propyl | 4-Methyl-3-cyclohexen-1-yl | 4-F | 0.95(t, 3H); 4.35(m, 4H); 5.35<br>(bs, 1H); 7.05(m, 2H); 7.55(m, 2H);<br>8.10(s, 1H) |
| 2.71 | Methyl | Tetrahydropyran-4-yl | 4-F | 2.30(s, 3H); 4.35(m, 4H); 7.05<br>(m, 2H); 7.55(m, 2H); 8.10(s, 1H) |
| 2.72 | Propyl | Tetrahydrofuran-3-yl | 4-F | 0.95(t, 3H); 4.35(m, 4H); 7.05<br>(m, 2H); 7.55(m, 2H); 8.10(s, 1H) |
| 2.73 | Propyl | Cyclohexyl | 4-Cl | 0.95(t, 3H); 4.35(m, 4H); 7.30<br>(m, 2H); 7.50(m, 2H); 8.05(s, 1H) |
| 2.74 | Propyl | 1-Methylthio-1-cyclopropyl | 4-Cl | 0.75(m, 2H); 0.95(m.5H); 4.35<br>(m, 4H); 7.35(m, 2H); 7.50(m, 2H);<br>8.10(s, 1H) |

TABLE 3

$$\text{structure: } R^2\text{-substituted cyclohexenone with OH, C(R}^1\text{)=N-O-(CH}_2)_3\text{-O-N=CH-phenyl-X}_n \quad I$$

(W = —(CH$_2$)$_3$—)

| No. | R$^1$ | R$^2$ | X$_n$ | Phys. data ($^1$H-NMR [ppm], m.p. [°C.]) |
|---|---|---|---|---|
| 3.01 | Ethyl | Tetrahydrothiopyran-3-yl | — | |
| 3.02 | Propyl | Tetrahydrothiopyran-3-yl | — | |
| 3.03 | Ethyl | Tetrahydropyran-3-yl | — | |
| 3.04 | Propyl | Tetrahydropyran-3-yl | — | |
| 3.05 | Ethyl | Tetrahydropyran-4-yl | — | |
| 3.06 | Propyl | Tetrahydropyran-4-yl | — | |
| 3.07 | Ethyl | Tetrahydrothiopyran-3-yl | 4-Cl | 1.15(t, 3H); 4.15–4.35(2m, 4H); 7.35(m, 2H); 7.50(m, 2H); 8.05 (s, 1H) |
| 3.08 | Propyl | Tetrahydrothiopyran-3-yl | 4-Cl | 0.95(t, 3H); 4.10–4.35(2m, 4H); 7.35(m, 2H); 7.55(m, 2H); 8.05 (s, 1H) |
| 3.09 | Ethyl | Tetrahydropyran-3-yl | 4-Cl | |
| 3.10 | Propyl | Tetrahydropyran-3-yl | 4-Cl | 0.95(t, 3H); 4.15–4.35(2m, 4H); 7.35(m, 2H); 7.50(m, 2H); 8.05 (s, 1H) |
| 3.11 | Ethyl | Tetrahydropyran-4-yl | 4-Cl | 1.15(t, 3H); 4.15–4.35(2m, 4H); 7.35(m, 2H); 7.45(m, 2H); 8.05 (s, 1H) |
| 3.12 | Propyl | Tetrahydropyran-4-yl | 4-Cl | 0.95(t, 3H); 4.15–4.35(2m, 4H); 7.35(m, 2H); 7.50(m, 2H); 8.05 (s, 1H) |
| 3.13 | Ethyl | Tetrahydrothiopyran-3-yl | 4-F | 1.15(t, 3H); 4.15–4.35(2m, 4H); 7.05(m, 2H); 7.55(m, 2H); 8.05 (s, 1H) |
| 3.14 | Propyl | Tetrahydrothiopyran-3-yl | 4-F | 0.95(t, 3H); 4.10–4.35(2m, 4H); 7.05(m, 2H); 7.55(m, 2H); 8.05 (s, 1H) |
| 3.15 | Ethyl | Tetrahydropyran-3-yl | 4-F | |
| 3.16 | Propyl | Tetrhydropyran-3-yl | 4-F | 0.95(t, 3H); 4.15–4.35(2m, 4H); 7.05(m, 2H); 7.55(m, 2H); 8.05 (s, 1H) |
| 3.17 | Ethyl | Tetrahydropyran-4-yl | 4-F | 1.15(t, 3H); 4.15–4.35(2m, 4H); 7.05(m, 2H); 7.55(m, 2H); 8.05 (s, 1H) |
| 3.18 | Propyl | Tetrahydropyran-4-yl | 4-F | 0.95(t, 3H); 4.20–4.35(2m, 4H); 7.05(m, 2H); 7.55(m, 2H); 8.05 (s, 1H) |
| 3.19 | Ethyl | Tetrahydrothiopyran-3-yl | 2,4-Cl$_2$ | 1.15(t, 3H); 4.10–4.35(2m, 4H); 7.25(m, 1H); 7.35(m, 1H); 8.40 (s, 1H) |
| 3.20 | Propyl | Tetrahydrothiopyran-3-yl | 2,4-Cl$_2$ | 0.95(t, 3H); 4.15–4.35(2m, 4H); 7.25(m, 1H); 7.35(m, 1H); 8.40 (s, 1H) |
| 3.21 | Ethyl | Tetrahydropyran-3-yl | 2,4-Cl$_2$ | |
| 3.22 | Propyl | Tetrahydropyran-3-yl | 2,4-Cl$_2$ | 0.95(t, 3H); 4.15–4.35(2m, 4H); 7.25(m, 1H); 7.40(m, 1H); 8.40 (s, 1H) |
| 3.23 | Ethyl | Tetrahydropyran-4-yl | 2,4-Cl$_2$ | 1.15(t, 3H); 4.15–4.35(2m, 4H); 7.25(m, 1H); 7.40(m, 1H); 8.40 (s, 1H) |
| 3.24 | Propyl | Tetrahydropyran-4-yl | 2,4-Cl$_2$ | 0.95(t, 3H); 4.15–4.35(2m, 4H); 7.25(m, 1H); 7.40(m, 1H); 8.40 (s, 1H) |
| 3.25 | Ethyl | Tetrahydrothiopyran-3-yl | 3,4-Cl$_2$ | |
| 3.26 | Propyl | Tetrahydrothiopyran-3-yl | 3,4-Cl$_2$ | |
| 3.27 | Ethyl | Tetrahydropyran-3-yl | 3,4-Cl$_2$ | |
| 3.28 | Propyl | Tetrahydropyran-3-yl | 3,4-Cl$_2$ | |
| 3.29 | Ethyl | Tetrahydropyran-4-yl | 3,4-Cl$_2$ | |
| 3.30 | Propyl | Tetrahydropyran-4-yl | 3,4-Cl$_2$ | |
| 3.31 | Ethyl | Tetrahydrothiopyran-3-yl | 4-NO$_2$ | |
| 3.32 | Propyl | Tetrahydrothiopyran-3-yl | 4-NO$_2$ | |
| 3.33 | Ethyl | Tetrahydropyran-3-yl | 4-NO$_2$ | |
| 3.34 | Propyl | Tetrahydropyran-3-yl | 4-NO$_2$ | |
| 3.35 | Ethyl | Tetrahydropyran-4-yl | 4-NO$_2$ | |
| 3.36 | Propyl | Tetrahydropyran 4-yl | 4-NO$_2$ | |

TABLE 3-continued $$\underset{(W = -(CH_2)_3-)}{R^2 \diagup \underset{O}{\overset{OH}{\diagdown}} \overset{N-O-(CH_2)_3-O-N=CH}{\underset{R^1}{\diagup}} \diagdown \underset{}{\diagup} X_n} \quad I$$

| No. | R¹ | R² | $X_n$ | Phys. data (¹H-NMR [ppm], m.p. [°C.]) |
|---|---|---|---|---|
| 3.37 | Propyl | 2-(Ethylthio)-1-propyl | — | |
| 3.38 | Propyl | 2-(Ethylthio)-1-propyl | 4-Cl | 0.95(t, 3H); 4.15–4.35(2m, 4H); 7.35(m, 2H); 7.50(m, 2H); 8.05 (s, 1H) |
| 3.39 | Propyl | 2-(Ethylthio)-1-propyl | 4-F | 0.95(t, 3H); 4.15–4.35(2m, 4H); 7.05(m, 2H); 7.55(m, 2H); 8.05 (s, 1H) |
| 3.40 | Propyl | 2-(Ethylthio)-1-propyl | 2,4-Cl₂ | 0.95(t, 3H); 4.10–4.35(2m, 4H); 7.25(m, 1H); 7.35(m, 1H); 7.80 (m, 1H); 8.40(s, 1H) |
| 3.41 | Propyl | 2-(Ethylthio)-1-propyl | 3,4-Cl₂ | |
| 3.42 | Ethyl | 2,4,6-Trimethylphenyl | — | |
| 3.43 | Ethyl | 2,4,6-Trimethylphe,yl | 4-Cl | |
| 3.44 | Ethyl | 2,4,6-Trimethylphenyl | 4-F | |
| 3.45 | Ethyl | 2,4,6-Trimethylphenyl | 2,4-Cl₂ | |
| 3.46 | Ethyl | 2,4,6-Trimethylphenyl | 3,4-Cl₂ | |
| 3.47 | Ethyl | 4-(Prop-2-ynyloxy)phenyl | — | |
| 3.48 | Ethyl | 4-(Prop-2-ynyloxy)phenyl | 4-Cl | |
| 3.49 | Ethyl | 4-(Prop-2-ynyloxy)phenyl | 4-F | |
| 3.50 | Ethyl | 4-(Prop-2-ynyloxy)phenyl | 2,4-Cl₂ | |
| 3.51 | Ethyl | 4-(Prop-2-ynyloxy)phenyl | 3,4-Cl₂ | |
| 3.52 | Ethyl | 1-Methylthio-1-cyclopropyl | — | |
| 3.53 | Ethyl | 1-Methylthio-1-cyclopropyl | 4-Cl | 0.75(m, 2H); 0.95(m, 2H); 1.15 (t, 3H); 4.10–4.35(2m, 4H); 7.35 (m, 2H); 7.50(m, 2H); 8.05(s, 1H) |
| 3.54 | Ethyl | 1-Methylthio-1-cyclopropyl | 4-F | 0.75(m, 2H); 0.95(m, 2H); 1.15 (t, 3H); 4.10–4.35(2m, 4H); 7.05 (m, 2H); 7.55(m, 2H); 8.05(s, 1H) |
| 3.55 | Ethyl | 1-Methylthio-1-cyclopropyl | 2,4-Cl₂ | 0.75(m,, 2H); 0.95(m, 2H); 1.15 (t, 3H); 4.10–4.35(2m, 4H); 7.25 (m, 1H); 7.35(m, 1H); 7.80(m, 1H); 8.40(s, 1H) |
| 3.56 | Ethyl | 1-Methylthio-1-cyclopropyl | 3,4-Cl₂ | |
| 3.57 | Ethyl | 1,3-Dimethylpyrazol-5-yl | — | |
| 3.58 | Ethyl | 1,3-Dimethylryrazol-5-yl | 4-Cl | |
| 3.59 | Ethyl | 1,3-Dimethylpyrazol-5-yl | 4-F | |
| 3.60 | Ethyl | 1,3-Dimethylpyrazol-5-yl | 2,4-Cl₂ | |
| 3.61 | Ethyl | 1,3-Dimethylpyrazol-5-yl | 3,4-Cl₂ | |
| 3.62 | Propyl | 3-Isopropylisoxazol-5-yl | — | |
| 3.63 | Propyl | 3-Isopropylisoxazol-5-yl | 4-Cl | |
| 3.64 | Propyl | 3-Isopropylisoxazol-5-yl | 4-F | |
| 3.65 | Propyl | 3-Isopropylisoxazol-5-yl | 2,4-Cl₂ | |
| 3.66 | Propyl | 3-Isopropylisoxazol-5-yl | 3,4-Cl₂ | |
| 3.67 | Propyl | 1-Methylthio-1-cyclopropyl | 4-F | 0.75(m, 2H); 0.95(m, 5H); 4.10–4.35(2m, 4H); 7.05(m, 2H); 7.55(m, 2H); 8.05(s, 1H) |
| 3.68 | Propyl | 1-Methylthio-1-cyclopropyl | 2,4-Cl₂ | 0.75(m, 2H); 0.95(m, 5H); 4.10–4.35(2m, 4H); 3.25(m, 1H); 7.35(m, 1H); 7.80(m, 1H); 8.40 (s, 1H) |

TABLE 4

Structure I: cyclohexenone with OH, R², C-R¹, =N-O-(CH₂)₄-O-N=CH-phenyl-Xₙ

(W = —(CH₂)₄—)

| No. | R¹ | R² | Xₙ | Phys data (¹H-NMR [ppm], m.p. [°C.]) |
|---|---|---|---|---|
| 4.01 | Ethyl | Tetrahydrothiopyran-3-yl | — | 1.05(m, 3H); 4.15(m, 2H); 4.22(m, 2H); 7.20(m, 3H); 7.35(m, 2H); 8.05(s, 1H) |
| 4.02 | Propyl | Tetrahydrothiopyran-3-yl | — | 0.95(t, 3H); 4.05(m, 2H); 4.20(m, 2H); 7.35(m, 3H); 7.55(m, 2H); 8.10(s, 1H) |
| 4.03 | Ethyl | Tetrahydropyran-3-yl | — | |
| 4.04 | Propyl | Tetrahydropyran-3-yl | — | |
| 4.05 | Ethyl | Tetrahydropyran-4-yl | — | 1.15(t, 3H); 3.90–4.30(m, 4H); 7.35 (m, 3H); 7.55(m, 2H); 8.05(s, 1H) |
| 4.06 | Propyl | Tetrahydropyran-4-yl | — | 0.95(t, 3H); 3.90–4.30(m, 4H); 7.35 (m, 3H); 7.55(m, 2H); 8.10(s, 1H) |
| 4.07 | Ethyl | Tetrahydrothiopyran-3-yl | 4-Cl | 55–57 |
| 4.08 | Propyl | Tetrahydrothiopyran-3-yl | 4-Cl | 67–69 |
| 4.09 | Ethyl | Tetrahydropyran-3-yl | 4-Cl | |
| 4.10 | Propyl | Tetrahydropyran-3-yl | 4-Cl | |
| 4.11 | Ethyl | Tetrahydropyran-4-yl | 4-Cl | 1.15(t, 3H); 3.90–4.30(m, 4H); 7.50 (m, 2H); 7.65(m, 2H); 8.00(s, 1H) |
| 4.12 | Propyl | Tetrahydropyran-4-yl | 4-Cl | 80–82 |
| 4.13 | Ethyl | Tetrahydrothiopyran-3-yl | 4-F | 46–48 |
| 4.14 | Propyl | Tetrahydrothiopyran-3-yl | 4-F | 57–60 |
| 4.15 | Ethyl | Tetrahydropyran-3-yl | 4-F | |
| 4.16 | Propyl | Tetrahydropyran-3-yl | 4-F | |
| 4.17 | Ethyl | Tetrahydropyran-4-yl | 4-F | 47–50 |
| 4.18 | Propyl | Tetrahydropyran-4-yl | 4-F | 63–64 |
| 4.19 | Ethyl | Tetrahydrothiopyran-3-yl | 2,4-Cl₂ | 1.15(t, 3H); 4.05(m, 2H); 4.20(m, 2H); 7.25(m, 1H); 7.35(m, 1H); 7.80(m, 1H); 18.40(s, 1H) |
| 4.20 | Propyl | Tetrahydrothiopyran-3-yl | 2,4-Cl₂ | 0.95(t, 3H); 4.05(m, 2H); 4.20(m, 2H); 7.25(m, 1H); 7.35(m, 1H); 7.80(m, 1H); 8.40(s, 1H) |
| 4.21 | Ethyl | Tetrahydropyran-3-yl | 2,4-Cl₂ | |
| 4.22 | Propyl | Tetrahydropyran-3-yl | 2,4-Cl₂ | |
| 4.23 | Ethyl | Tetrahydropyran-4-yl | 2,4-Cl₂ | 86–87 |
| 4.24 | Propyl | Tetrahydropyran-4-yl | 2,4-Cl₂ | 0.95(t, 3H) ; 3.90–4.30(m, 4H); 7.25 (m, 1H); 7.35(m, 1H); 7.80(m, 1H); 8.40 (s, 1H) |
| 4.25 | Ethyl | Tetrahydrothiopyran-3-yl | 3,4-Cl₂ | |
| 4.26 | Propyl | Tetrahydrothiopyran-3-yl | 3,4-Cl₂ | |
| 4.27 | Ethyl | Tetrahydropyran-3-yl | 3,4-Cl₂ | |
| 4.28 | Propyl | Tetrahydropyran-3-yl | 3,4-Cl₂ | |
| 4.29 | Ethyl | Tetrahydropyran-4-yl | 3,4-Cl₂ | |
| 4.30 | Propyl | Tetrahydropyran-4-yl | 3,4-Cl₂ | |
| 4.31 | Ethyl | Tetrahydrothiopyran-3-yl | 4-NO₂ | |
| 4.32 | Propyl | Tetrahydrothiopyran-3-yl | 4-NO₂ | |
| 4.33 | Ethyl | Tetrahydropyran-3-yl | 4-NO₂ | |
| 4.34 | Propyl | Tetrahydropyran-3-yl | 4-NO₂ | |
| 4.35 | Ethyl | Tetrahydropyran-4-yl | 4-NO₂ | |
| 4.36 | Propyl | Tetrahydropyran-4-yl | 4-NO₂ | |
| 4.37 | Propyl | 2-(Ethylthio)-1-propyl | | 1.25(d+t, 6H); 4.05(m, 2H); 4.20 (m, 2H); 7.30(m, 3H); 7.55(m, 2H); 8.05 (s, 1H) |
| 4.38 | Propyl | 2-(Ethylthio)-1-propyl | 4-Cl | 1.25(d+t, 6H); 4.05(m, 2H); 4.20 (m, 2H); 7.30(m, 2H); 7.50(m, 2H); 8.05 (s, 1H) |
| 4.39 | Propyl | 2-(Ethylthio)-1-propyl | 4-F | 1.15(d+t, 6H); 4.10(m, 2H); 4.20 (m, 2H); 7.05(m, 2H); 7.55(m, 2H); 8.05 (s, 1H) |
| 4.40 | Propyl | 2-(Ethylthio)-1-propyl | 2,4-Cl₂ | 1.25(d+t, 6H); 4.05(m, 2H); 4.20 (m, 2H); 7.25(m, 1H); 7.35(m, 1H); 7.70 (m, 1H); 8.40(s, 1H) |
| 4.41 | Propyl | 2-(Ethylthio)-1-propyl | 3,4-Cl₂ | |
| 4.42 | Ethyl | 2,4,6-Trimethylphenyl | — | |
| 4.43 | Ethyl | 2,4,6-Trimethylphenyl | 4-Cl | |
| 4.44 | Ethyl | 2,4,6-Trimethylphenyl | 4-F | |
| 4.45 | Ethyl | 2,4,6-Trimethylphenyl | 2,4-Cl₂ | |
| 4.46 | Ethyl | 2,4,6-Trimethylphenyl | 3,4-Cl₂ | |
| 4.47 | Ethyl | 4-(Prop-2-ynyloxy)phenyl | — | |
| 4.48 | Ethyl | 4-(Prop-2-ynyloxy)phenyl | 4-Cl | |

TABLE 4-continued $$\underset{(W = -(CH_2)_4-)}{R^2 - \overset{OH}{\underset{O}{\bigcirc}} - \overset{N-O-(CH_2)_4-O-N=CH}{\underset{R^1}{C}} - \underset{}{\bigcirc} - X_n} \quad I$$

| No. | R¹ | R² | $X_n$ | Phys data (¹H-NMR [ppm], m.p. [°C.]) |
|---|---|---|---|---|
| 4.49 | Ethyl | 4-(Prop-2-ynyloxy)phenyl | 4-F | |
| 4.50 | Ethyl | 4-(Prop-2-ynyloxy)phenyl | 2,4-Cl₂ | |
| 4.51 | Ethyl | 4-(Prop-2-ynyloxy)phenyl | 3,4-Cl₂ | |
| 4.52 | Ethyl | 1-Methylthio-1-cyclopropyl | — | |
| 4.53 | Ethyl | 1-Methylthio-1-cyclopropyl | 4-Cl | |
| 4.54 | Ethyl | 1-Methylthio-1-cyclopropyl | 4-F | |
| 4.55 | Ethyl | 1-Methylthio-1-cyclopropyl | 2,4-Cl₂ | |
| 4.56 | Ethyl | 1-Methylthio-1-cyclopropyl | 3,4-Cl₂ | |
| 4.57 | Ethyl | 1,3-Dimethylpyrazol-5-yl | — | |
| 4.58 | Ethyl | 1,3-Dimethylpyrazol-5-yl | 4-Cl | |
| 4.59 | Ethyl | 1,3-Dimethylpyrazol-5-yl | 4-F | |
| 4.60 | Ethyl | 1,3-Dimethylpyrazol-5-yl | 2,4-Cl₂ | |
| 4.61 | Ethyl | 1,3-Dimethylpyrazol-5-yl | 3,4-Cl₂ | |
| 4.62 | Propyl | 3-Isopropylisoxazol-5-yl | — | |
| 4.63 | Propyl | 3-Isopropylisoxazol-5-yl | 4-Cl | |
| 4.64 | Propyl | 3-Isopropylisoxazol-5-yl | 4-F | |
| 4.65 | Propyl | 3-Isopropylisoxazol-5-yl | 2,4-Cl₂ | |
| 4.66 | Propyl | 3-Isopropylisoxazol-5-yl | 3,4-Cl₂ | |

The cyclohexenone oxime ethers I are suitable, both as isomer mixtures and in the form of the pure isomers, as herbicides especially for combating plants from the Gramineae species. They are generally well tolerated and are thus selective in broadleaved crops and in monocotyledons not belonging to the Gramineae. Some of the cyclohexenone oxime ethers I are also suitable for selectively combating unwanted grasses in Gramineae.

The cyclohexenone oxime ethers I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I are generally suitable for the preparation of solutions, emulsions, pastes and oil dispersions to be sprayed direct. Examples of suitable inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and Vegetable products such as grain meals, bark meal, wood meal, and nutshell meal, cellulosic powders, etc.

The formulations contain from 0.01 to 95, and preferably 0.5 to 90, % by weight of active ingredient. The active ingredients are used in a purity of 90 to 100, and preferably 95 to 100, % (according to the NMR spectrum).

Examples of formulations are as follows:

I. A solution of 90 parts by weight of compound no. 2.01 and 10 parts by weight of N-methyl-α-pyrrolidone, which is suitable for application in the form of very fine drops.

II. A mixture of 20 parts by weight of compound no. 2.03, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in 100,000 parts by weight of water, an aqueous dispersion containing 0.02wt % of the active ingredient is obtained.

III. An aqueous dispersion of 20 parts by weight of compound no. 2.37, 40 parts by weight of cyglohexanone, 30 parts by weight of isobutanol, 20 parts by weight of the adduct of 40 moles of ethylene oxide and 1 mole of castor oil. A mixture of this dispersion with 100,000 parts by weight of water contains 0.02wt % of the active ingredient.

IV. An aqueous dispersion of 20 parts by weight of compound no. 2.43, 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. The mixture of this dispersion with 100,000 parts by weight of water contains 0.02wt % of the active ingredient.

V. A hammer-milled mixture of 80 parts by weight of compound no. 2.64, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in 20,000 parts by weight of water, a spray liquor containing 0.1wt % of the active ingredient is obtained.

VI. An intimate mixture of 3 parts by weight of compound no. 2.70 and 97 parts by weight of particulate kaolin. The dust contains 3wt % of the active ingredient.

VII. An intimate mixture of 30 parts by weight of compound no. 2.73, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 4.07, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 4.38, 2 parts by weight of the calcium salt of dodecylbenzenesulfonic acid, 8 parts by weight of a fatty alcohol polyglycol ether, 20 parts by weight of the sodium salt of a phenolsulfonic acid-urea-formaldehyde condensate and 68 parts by weight of a paraffinic mineral oil.

X. A hammer-milled mixture of 10 parts by weight of compound no. 4.40, 4 parts by weight of the sodium salt of diisobutylnaphthalene-α-sulfonic acid, 20 parts by weight of the sodium salt of a lignin-sulfonic acid obtained from a sulfite waste liquor, and 38 parts by weight of powdered silica gel. By finely dispersing the mixture in 10,000 parts by weight of water, a spray liquor containing 0.1wt % of the active ingredient is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3, preferably 0.01 to 1, kg of active ingredient per hectare.

In view of the numerous application methods possible, the cyclohexenone oxime ethers I or agents containing them may be used in a large number of crops for removing unwanted plants. Those which follow are given by way of example:

| | |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Brassica napus* var. *napus* | rapeseed |
| *Brassica napus* var. *napobrassica* | swedes |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus sinensis* | orange trees |
| *Coffea arabica* (*Coffea canephora*, *Coffea liberica*) | coffee plants |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum*, *Gossypium herbaceum*, *Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Musa* spp. | banana plants |
| *Nicotiana tabacum* (*N. rustica*) | tobacco |
| *Olea europaea* | olive trees |
| *Oryza sativa* | rice |
| *Phaseolus lunatus* | limabeans |
| *Phaseolus vulgaris* | snapbeans, green beans, dry beans |
| *Picea abies* | Norway spruce |
| *Pinus* spp. | pine trees |
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ricinus communis* | castor-oil plants |
| *Saccharum officinarum* | sugar cane |
| *Secale cereale* | rye |
| *Solanum tuberosum* | Irish potatoes |
| *Sorghum bicolor* (*s. vulgare*) | sorghum |
| *Theobroma cacao* | cacao plants |
| *Trifolium pratense* | red clover |
| *Triticum aestivum* | wheat |
| *Triticum durum* | wheat |
| *Vicia faba* | tick beans |
| *Vitis vinifera* | grapes |
| *Zea mays* | Indian corn, sweet corn, maize |

To increase the spectrum of action and to achieve synergistic effects, the cyclohexenone oxime ethers I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives bearing in the 2-position for example a carboxy or carbimino group, quinolinecarboxylic acids, imidazolinones, sulfonamides, sulfonylureas, (hetero)-aryloxyphenoxypropionic acids and salts, esters, amides thereof, etc.

It may also be useful to apply the compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

Use examples

The herbicidal action of the unsaturated cyclohexenone oxime ethers of the formula I is demonstrated in greenhouse experiments:

The vessels employed were plastic flowerpots filled with a sandy loam containing about 3.0% humus. The seeds of the test plants were sown separately, according to species.

For the preemergence treatment, the active ingredients, emulsified or suspended in water, were applied immediately after the seeds had been sown, and sprayed through finely distributing nozzles. The vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, plants were used which had been sown in the pots and grown there, or they were grown separately as seedlings and transplanted to the pots a few days before treatment. The plants were grown, depending on growth form, to a height of 3 to 15 cm before being treated with the compounds, suspended or emulsified in water. The application rate for postemergence treatment was 0.03 kg/ha.

The pots were set up at temperatures, specific to their species, of 20° to 35° C., or 10° to 25° C. The experiments were run for from 2 to 4 weeks. During this period the plants were tended and their reactions to the various treatments assessed.

The assessment scale was 0 to 100, 100 denoting non-emergence or complete destruction of at least the visible plant parts, and 0 denoting no damage or normal growth.

The plants used in the greenhouse experiments were Echinochloa crus-galli, Oryza sativa, Setaria italica and Setaria viridis.

The results show that unwanted grasses can be excellently controlled in rice with compound no. 2.13.

We claim:

1. A cyclohexenone oxime ether of the formula I

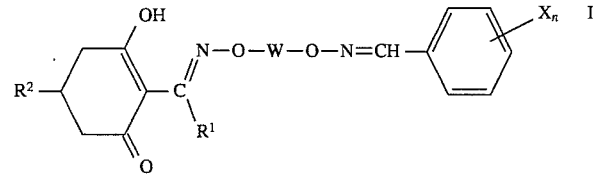

where the substituents have the following meaning:

$R^1$ is a $C_1$–$C_6$-alkyl group;

W is an unsubstituted or $C_1$–$C_3$-alkyl-substituted $C_2$–$C_4$-alkylene chain;

X is nitro, cyano, halogen, $C_1$–$C_4$-alkyl or $C_1$–$C_1$-haloalkyl;

n is 0 or n is 1 to 3 when X is nitro, cyano, halogen, $C_1$–$C_4$-alkyl or $C_1$–$C_4$-haloalkyl, where the radicals X are identical or different when n is 2 or 3, and n can additionally be 4 or 5 if all the X's are halogen;

$R^2$ is a $C_1$–$C_4$-alkoxy-$C_1$–$C_6$-alkyl or $C_1$–$C_4$-alkylthio-$C_1$–$C_6$alkyl group, a $C_3$–$C_7$-cycloalkyl or a $C_5$–$C_7$-cycloalkenyl group, these groups being unsubstituted or bearing from one to three substituents selected from the group consisting of $C_1$–$C_4$-alkyl, $C_1$–$C_4$-alkoxy, $C_1$–$C_4$-alkylthio, $C_1$–$C_4$-haloalkyl, hydroxyl and halogen; a 5-membered saturated heterocycle which consists of one or two oxygen and/or sulfur atoms as heteroatoms and is unsubstituted or bears from one to three substituents selected from the group consisting of $C_1$–$C_4$-alkyl, $C_1$–$C_4$-alkoxy, $C_1$–$C_4$-alkylthio and $C_1$–$C_4$-haloalkyl; a 6- or 7-membered heterocycle having one or two non-adjacent oxygen and/or sulfur atoms as heteroatoms and which is saturated or mono- or diunsaturated and which is unsubstituted or bears from one to three substituents selected from the group consisting of hydroxyl, halogen, $C_1$–$C_4$-alkyl, $C_1$–$C_4$-alkoxy, $C_1$–$C_4$-alkylthio and $C_1$–$C_4$-haloalkyl; a 5-membered heteroaromatic containing one or two nitrogen atoms and an oxygen or sulfur atom and which is unsubstituted or bears from one to three substituents selected from the group consisting of halogen, cyano, $C_1$–$C_4$-alkyl, $C_1$–$C_4$-alkoxy, $C_1$–$C_4$-alkylthio, $C_1$–$C_4$-haloalkyl, $C_2$–$C_6$-alkenyl, $C_2$–$C_6$-alkenyloxy and $C_1$–$C_4$-alkoxy-$C_1$–$C_4$-alkyl; phenyl or pyridyl, these groups being unsubstituted or bearing from one to three substituents selected from the group consisting of halogen, nitro, cyano, $C_1$–$C_4$-alkyl, $C_1$–$C_4$-alkoxy, $C_1$–$C_4$-alkylthio, $C_1$–$C_4$-haloalkyl, $C_3$–$C_6$-alkenyloxy, $C_3$–$C_6$-alkynyloxy and an amino group —$NR^aR^b$, where $R^a$ is hydrogen, $C_1$–$C_4$-alkyl, $C_3$–$C_6$-alkenyl or $C_3$–$C_6$-alkynyl and $R^b$ is hydrogen, $C_1$–$C_4$-alkyl, $C_3$–$C_6$-alkenyl, $C_3$–$C_6$-alkynyl or $C_1$–$C_6$-acyl, or benzoyl which is unsubstituted or bears from one to three radicals selected from the group consisting of nitro, cyano, halogen, $C_1$–$C_4$-alkyl, $C_1$–$C_4$-alkoxy, $C_1$–$C_4$-alkylthio and $C_1$–$C_4$-haloalkyl and the agriculturally utilizable salts and esters of compounds I with $C_1$–$C_{10}$-carboxylic acids and inorganic acids.

2. A cyclohexenone oxime ether of the formula I as defined in claim 1 wherein

W is $C_2$–$C_4$-alkylene;

X is halogen;

n is 0 to 2; and $R^2$ is $C_1$–$C_4$-alkylthio-$C_1$–$C_1$-alkyl, $C_3$–$C_7$-cycloalkyl bearing a $C_1$–$C_4$-alkylthio group, or a 6-membered heterocycle having one oxygen or sulfur atom as heteroatom.

3. A cyclohexenone oxime ether of the formula I as defined in claim 1 wherein

W is $C_2$–$C_4$-alkylene;

X is chlorine or fluorine;

n is 0 to 2; and $R^2$ is 2-(ethylthio)-prop-1-yl, 1-methylthio-cycloprop-1-yl, tetrahydropyran-3-yl, tetrahydropyran-4-yl or tetrahydrothiopyran-3-yl.

4. A herbicidal composition containing inert additives and at least one cyclohexenone oxime ether of the formula I as set forth in claim 1.

5. A method of combating the growth of unwanted plants, wherein a herbicidally effective amount of a cyclohexenone oxime ether I as set forth in claim 1 is allowed to act on the plants, their habitat or their seed.

6. Hydroxylamines of the formula III

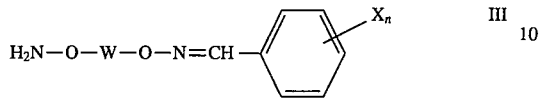

where

W is an unsubstituted or $C_1$–$C_3$-alkyl-substituted $C_2$-$C_4$-alkylene chain;

X is nitro, cyano, halogen, $C_1$–$C_4$-alkyl or $C_1$–$C_1$–haloalkyl; and n is 0 or n is 1 to 3 when X is nitro, cyano, halogen, $C_1$–$C_4$-alkyl or $C_1$–$C_4$-haloalkyl, where the radicals X are identical or different when n is 2 or 3, and n can additionally be 4 or 5 if all the X's are halogen.

* * * * *

UNITED STATES PATENT AND TRADEMARK OFFICE
CERTIFICATE OF CORRECTION

PATENT NO.: 5,496,792

DATED: March 5, 1996

INVENTOR(S): MISSLITZ et al.

It is certified that error appears in the above-identified patent and that said Letters Patent is hereby corrected as shown below:

Column 26, claim 2, line 56, "$C_1$-$C_4$-alkylthio-$C_1$-$C_1$-alkyl" should read --$C_1$-$C_4$-alkylthio-$C_1$-$C_6$-alkyl--.

Column 28, claim 6, line 6, "$C_1$-$C_1$-haloalkyl" should read --$C_1$-$C_4$-haloalkyl--.

Signed and Sealed this

Eleventh Day of February, 1997

BRUCE LEHMAN

Attesting Officer     Commissioner of Patents and Trademarks